(12) United States Patent
Guy

(10) Patent No.: US 11,851,263 B2
(45) Date of Patent: Dec. 26, 2023

(54) DENTAL MATERIAL CONTAINER

(71) Applicant: GC Corporation, Shizuoka (JP)

(72) Inventor: Verstraeten Guy, Tokyo (JP)

(73) Assignee: GC Corporation, Shizuoka (JP)

( * ) Notice: Subject to any disclaimer, the term of this patent is extended or adjusted under 35 U.S.C. 154(b) by 675 days.

(21) Appl. No.: 17/041,163

(22) PCT Filed: Dec. 6, 2018

(86) PCT No.: PCT/JP2018/044951
§ 371 (c)(1),
(2) Date: Sep. 24, 2020

(87) PCT Pub. No.: WO2019/187363
PCT Pub. Date: Oct. 3, 2019

(65) Prior Publication Data
US 2021/0009338 A1 Jan. 14, 2021

(30) Foreign Application Priority Data
Mar. 27, 2018 (JP) .................................. 2018-059438

(51) Int. Cl.
*B65D 83/04* (2006.01)
*A61K 6/802* (2020.01)
*A61C 19/10* (2006.01)

(52) U.S. Cl.
CPC .......... *B65D 83/0427* (2013.01); *A61C 19/10* (2013.01); *A61K 6/802* (2020.01); *A61C 2202/00* (2013.01); *B65D 2583/0472* (2013.01)

(58) Field of Classification Search
CPC ............ B65D 83/0481; B65D 83/0409; B65D 2583/0472

(Continued)

(56) References Cited

U.S. PATENT DOCUMENTS 2,705,576 A    4/1955 Amelio et al.
2,893,599 A *  7/1959 Kay .................... B65D 83/0409
                                                       221/281

(Continued)

FOREIGN PATENT DOCUMENTS

CA      3025278       11/2017
DE     102011009073    7/2012
FR      1098150        7/1955

OTHER PUBLICATIONS

International Search Report for PCT/JP2018/044951 dated Jan. 29, 2019.

(Continued)

*Primary Examiner* — Timothy R Waggoner
(74) *Attorney, Agent, or Firm* — IPUSA, PLLC

(57) ABSTRACT

A dental material container includes a cylindrical body that stores a dental material including a pair of opposing primary surfaces, and a rotatable cap covering the body. The cap includes an internal space capable of housing the dental material. The body includes a pair of first holders that are formed on an inner surface of the body to movably hold the primary surfaces of the dental material; the cap includes a pair of second holders formed inside of the cap to movably hold the primary surfaces of the dental material. When the cap is rotated in the circumferential direction relative to the body, a continuous space where the dental material is movable is formed by the first and second holders, the dental material located closest to the opening in the body moves into the cap, and the dental material moved into the cap is housed in the cap.

6 Claims, 14 Drawing Sheets

(58) Field of Classification Search
USPC .......................................................... 206/535
See application file for complete search history.

(56) References Cited

U.S. PATENT DOCUMENTS 3,166,216 A * 1/1965 Guarr ................. B65D 83/0409
221/289
3,245,589 A 4/1966 Temliak
4,971,203 A * 11/1990 Weinstein .......... B65D 83/0481
206/536

OTHER PUBLICATIONS

Brochure of "Ceramics for Dental Pressure Molding, Initial LiSi Press" Home Page of GC Corporation, [Searched on Jan. 26, 2018], Internet <URL: http://www.gcdental.co.jp/sys/data/item/doc/1465/> published on Mar. 22, 2016. With English Concise Explanation.

* cited by examiner

DENTAL MATERIAL CONTAINER

TECHNICAL FIELD

The present invention relates to a dental material container.

BACKGROUND ART

Prostheses such as a veneer crown, an inner core, and a bridge have been used as dental products (dental materials) for dental treatment. Such dental materials are manufactured in a dental laboratory using a ceramic material such as aluminum oxide or zirconium oxide, a metal, or an alloy. Among them, from the viewpoint of aesthetics, convenience, and durability, dental ceramic molded bodies shaped like tablets are used to produce dental materials.

The dental ceramic molded bodies can be used in a casting method called a lost wax method. In this casting method, on a plaster model (model) of a tooth obtained based on an impression (negative model) corresponding to the shape of an affected part in the oral cavity of a patient, a wax prosthetic model with the same outer shape as a prosthesis to be fixed to the affected part is formed using dental casting wax. After embedding the prosthetic model in an investment material and hardening the investment material, the prosthetic model is heated in an electric furnace to remove the prosthetic model. As a result, a void with the same internal shape as the outer shape of the prosthetic model is formed in the hardened investment material. Then, a dental ceramic molded body is pressed into the void of the heated investment material while applying pressure to the dental ceramic molded body to form a prosthesis with the same shape as the prosthetic model in the investment material. The investment material is broken to take out the prosthesis made of the dental ceramic and formed in the investment material.

Generally, dental ceramic molded bodies used to produce prostheses are placed and stored in a dental material container. FIG. 20 illustrates an example of a dental material container. As illustrated in FIG. 20, a dental material container 100 includes a container 101 shaped like a cylinder with a bottom. Dental ceramic molded bodies are placed in the container 101 and the container 101 is closed with a cap 102 such that the dental ceramic molded bodies are stored in the sealed container 101 (see, for example, Non-Patent document 1).

RELATED-ART DOCUMENT

Non-Patent Document

[Non-Patent Document 1] Brochure of "Ceramics for Dental Pressure Molding, Initial LiSi Press" Home Page of GC Corporation, [Searched on Jan. 26, 2018], Internet <URL: http://www.gcdental.co.jp/sys/data/item/doc/1465/>

DISCLOSURE OF INVENTION

Problems to be Solved by the Invention

However, with the dental material container 100 of the related art, because the cap 102 is securely fitted into the opening at one end of the container 101, it is necessary to pull out the cap 102 from the container 101 with a relatively strong force to take out the dental ceramic molded bodies from the dental material container 100. Therefore, when the cap 102 is strongly pulled out from the container 101 to open the container 101 and use a dental ceramic molded body at a dental laboratory, the dental ceramic molded body may pop out of the container 101, fall on, for example, a workbench or a floor, and break.

One aspect of the present invention aims to provide a dental material container from which a dental material can be easily taken out.

Means for Solving the Problems

In an aspect of the present invention, a dental material container includes a container body shaped like a cylinder with a bottom and configured to store a dental material that is shaped like a thick plate and includes a pair of opposing primary surfaces, and a cap formed to cover an opening at one end of the container body. The cap is provided on the container body such that the cap is rotatable in a circumferential direction of the container body and includes an internal space capable of housing the dental material; an outlet through which the dental material is taken out is formed in a side surface of the cap; the container body includes a pair of first holders that are formed on an inner surface of the container body to hold the primary surfaces of the dental material such that the dental material is movable; the cap includes a pair of second holders formed inside of the cap to hold the primary surfaces of the dental material such that the dental material is movable; and the dental material container is configured such that when the cap is rotated in the circumferential direction relative to the container body, a continuous space where the dental material is movable is formed by the first holders and the second holders, the dental material located closest to the opening in the container body moves into the cap, and the dental material moved into the cap is housed in the cap.

Advantageous Effect of the Invention

An aspect of the present invention provides a dental material container from which a dental material can be easily taken out.

DESCRIPTION OF EMBODIMENTS

Figure 1:
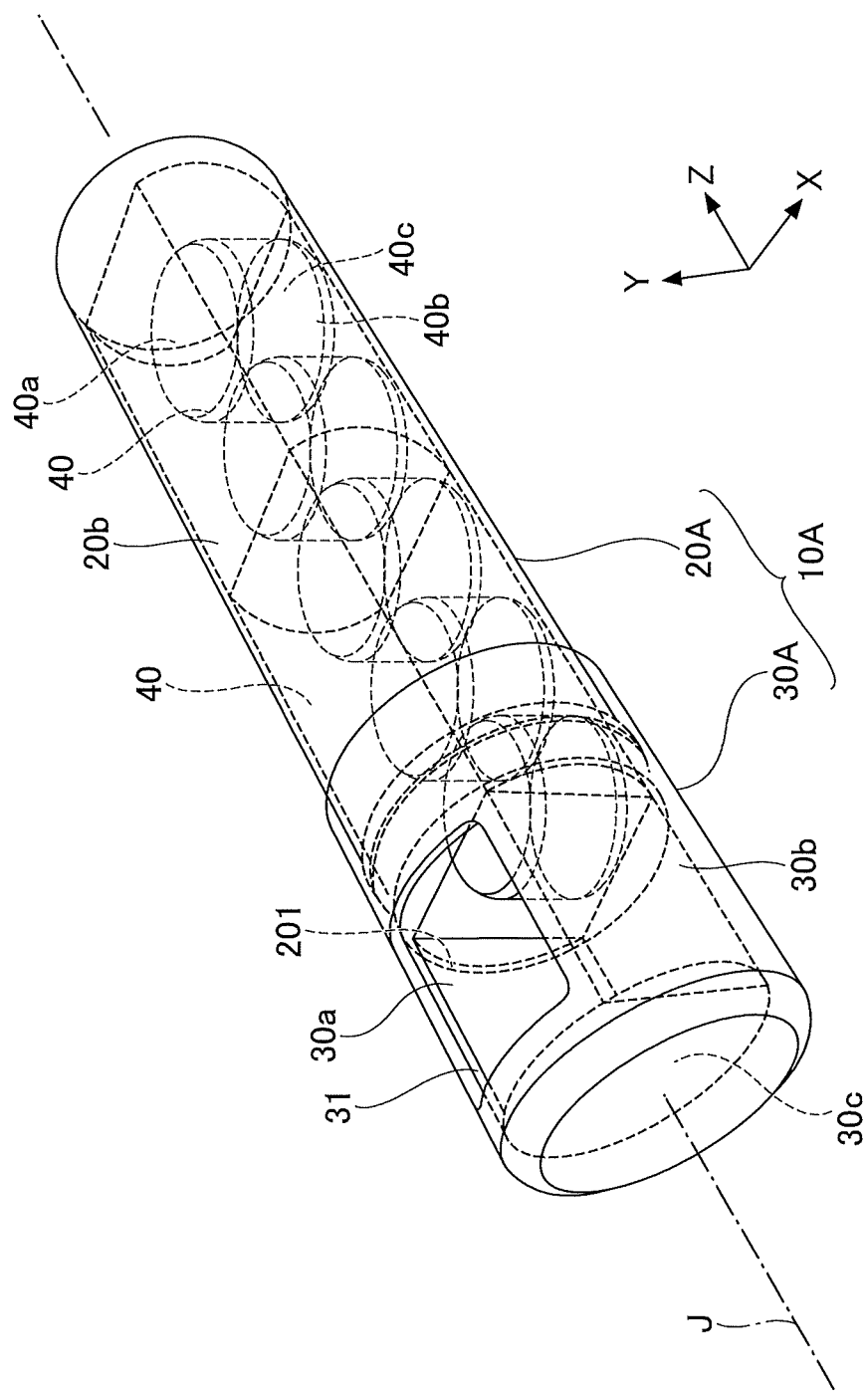
FIG. 1 is a perspective view of a dental material container according to a first embodiment.

Embodiments of the present invention are described below in detail. For easy understanding, the scale of each component in the drawings may differ from its actual scale. In the present application, a three-dimensional orthogonal coordinate system with three axial directions (X axis direction, Y axis direction, and Z axis direction) is used. The Z axis direction indicates a direction parallel to a central axis J of a dental material container, the X axis direction indicates one of two directions that are orthogonal to each other in a plane orthogonal to the central axis J, and the Y axis direction indicates the other one of the two directions.

First Embodiment

A dental material container according to a first embodiment is described. In the present embodiment, it is assumed that a dental material is a dental ceramic molded body (hereafter, simply referred to as a dental ceramic).

Figure 2:
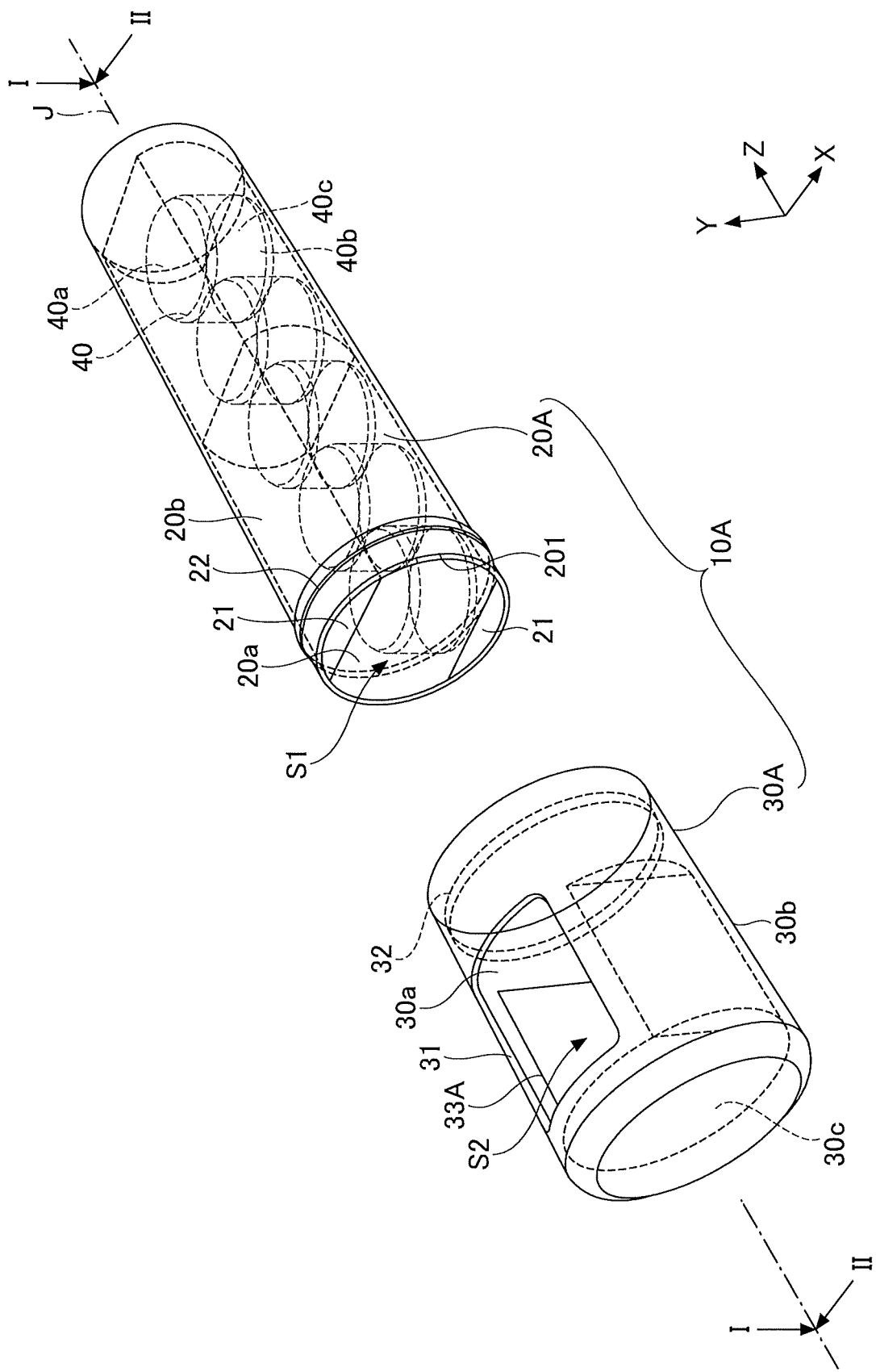
FIG. 2 is an exploded perspective view of a dental material container.
Figure 3:
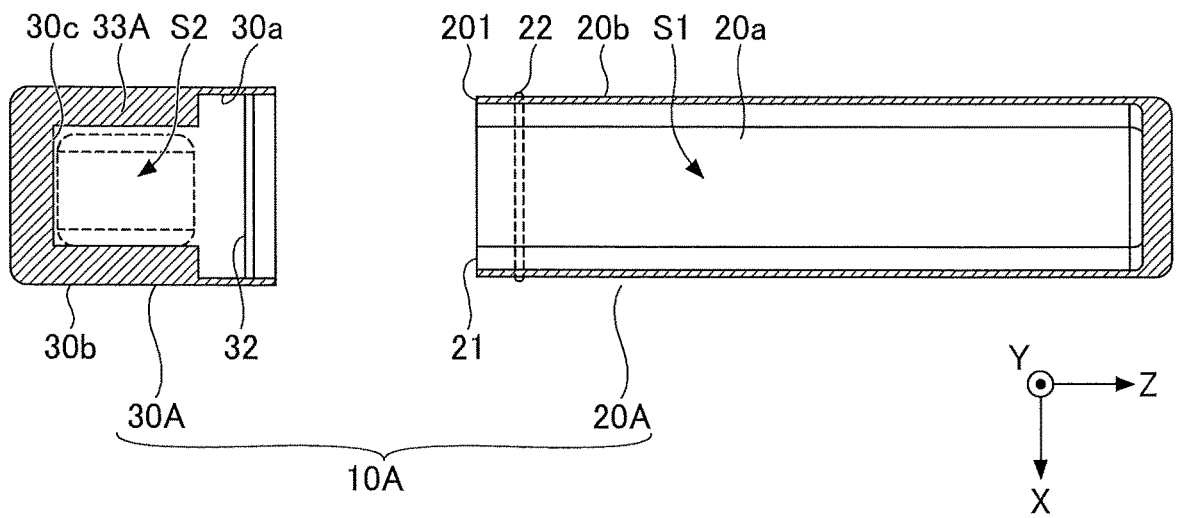
FIG. 3 is a cross-sectional view taken along line I-I of FIG. 2.
Figure 4:
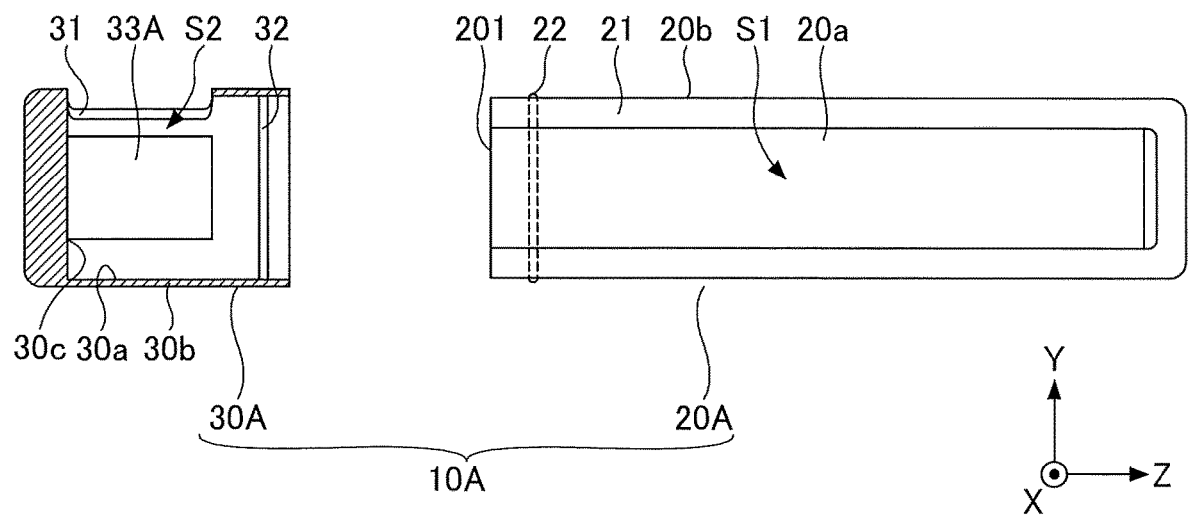
FIG. 4 is a cross-sectional view taken along line II-II of FIG. 2.
Figure 5:
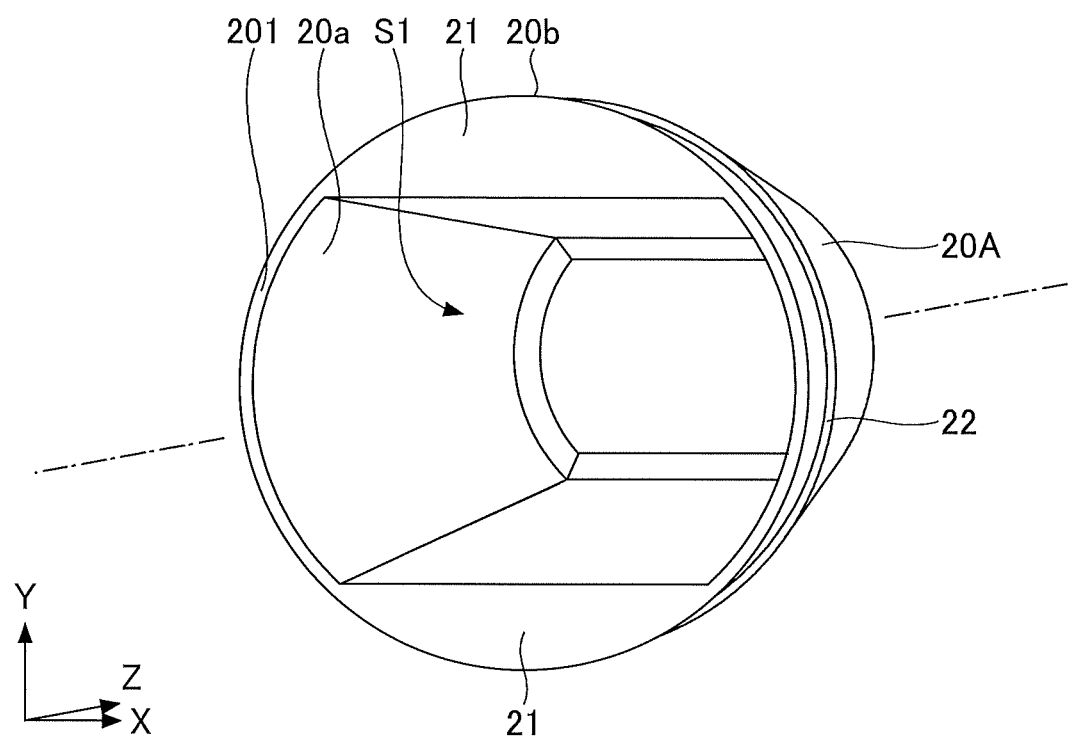
FIG. 5 is a perspective view of an inside of a container body.
Figure 6:
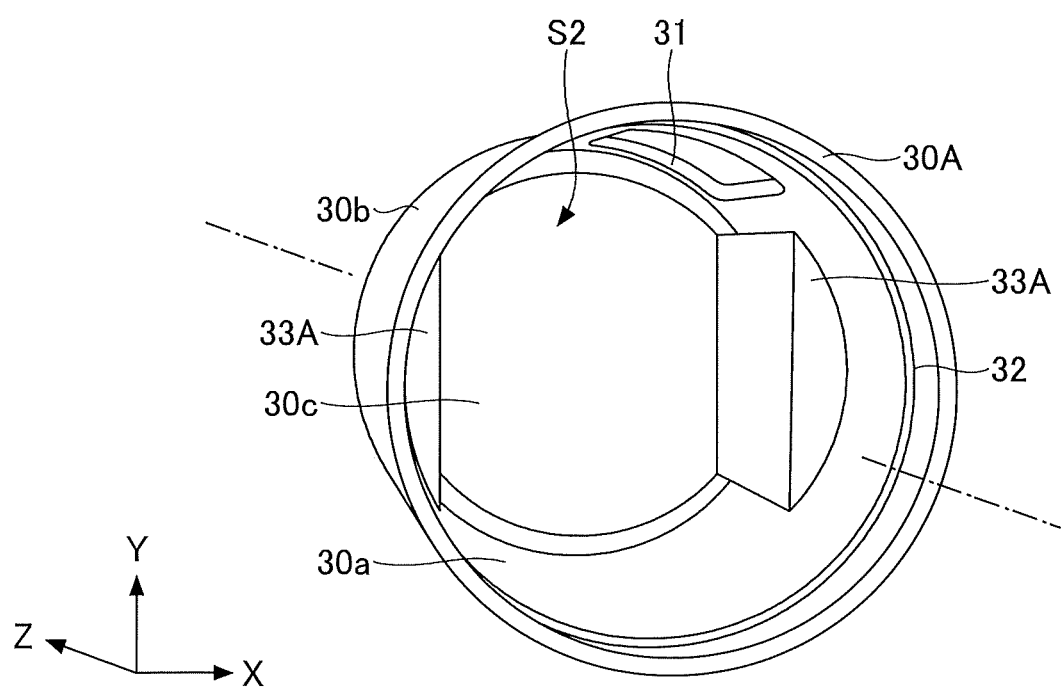
FIG. 6 is a perspective view illustrating an inside of a cap.

FIG. 1 is a perspective view of a dental material container according to the first embodiment, FIG. 2 is an exploded perspective view of the dental material container, FIG. 3 is a cross-sectional view taken along line I-I of FIG. 2, FIG. 4 is a cross-sectional view taken along line II-II of FIG. 2, FIG. 5 is a perspective view of an inside of a container body, and FIG. 6 is a perspective view of an inside of a cap. As illustrated in FIGS. 1 through 6, a dental material container 10A includes a container body 20A and a cap 30A.

The container body 20A is a container shaped like a cylinder with a bottom, and includes an opening 201 at one end (an end in the −Z axis direction). The container body 20A includes an internal space S1. The space S1 has a size that can house multiple dental ceramics 40. The dental ceramics 40 stored in the space S1 are arranged in the axial direction (the Z axis direction) of the container body 20A.

Each of the dental ceramics 40 is shaped like a thick plate and includes a pair of opposing primary surfaces 40a and 40b. The primary surfaces 40a and 40b have a circular shape in plan view. The edges of the primary surfaces 40a and 40b are chamfered. The dental ceramics 40 are stored in the container body 20A such that end faces 40c of adjacent dental ceramics 40 are in contact with each other.

The container body 20A is formed of a material having optical transparency. Examples of materials of the container body 20A include polyethylene terephthalate (PET), polyethylene naphthalate (PEN), polyether sulfone (PES), polyether imide (PEI), polyether ether ketone (PEEK), polyphenylene sulfide (PPS), polyarylate (PAR), polyimide (PI), polycarbonate (PC), cycloolefone (COP), cellulose acetate (TAC), and cellulose acetate propionate (CAP). One of these resins may be used alone, or two or more of the resins may be used in combination.

In the present embodiment, the container body 20A may have optical transparency to visible light (light having a wavelength of 380 to 780 nm) such that the shapes of the dental ceramics 40 in the container body 20A can be visually recognized from the outside. The container body 20A preferably has a high optical transmittance of visible light. For example, the optical transmittance of visible light is preferably greater than or equal to 60%, more preferably greater than or equal to 70%, and further preferably greater than or equal to 80%. The container body 20A is colorless. However, the container body 20A may have a color as long as it has optical transparency.

The container body 20A includes, on an inner surface 20a, a pair of first holders 21 that extend along the axial direction (the Z axis direction) of the container body 20A. The pair of first holders 21 are arranged on the inner surface 20a of the container body 20A to face each other. In the present embodiment, surfaces of the first holders 21 facing the primary surfaces 40a and 40b of the dental ceramic 40 are made flat to match the primary surfaces 40a and 40b. The dental ceramic 40 is placed between the first holders 21 in the container body 20A such that the pair of primary surfaces 40a and 40b of the dental ceramic 40 face the first holders 21. The pair of first holders 21 hold the primary surfaces 40a and 40b of the dental ceramic 40 such that the dental ceramic 40 is movable. The pair of first holders 21 and the container body 20A are formed as a monolithic component. However, the first holders 21 may be produced as components separate from the container body 20A and attached to the inner surface 20a of the container body 20A using, for example, a bonding material such as an adhesive or a double-sided tape.

The container body 20A includes a protrusion 22 on its side surface (outer surface) 20b. The protrusion 22 is formed on the outer surface 20b and has a circular shape that extends along the circumferential direction of the container body 20A. The protrusion 22 is positioned at a predetermined distance from the opening 201. The protrusion 22 is preferably positioned at a distance from the opening 201 that is within a range between 10% and 20% of the entire length of the container body 20A. With the protrusion 22 positioned at a distance within the above range, a state where the cap 30A is stably supported by the container body 20A can be maintained, and the cap 30A can be stably rotated in a state where the protrusion 22 is placed in a groove 32 of the cap 30A.

The cap 30A is shaped like a cylinder with a bottom, and is formed to cover the opening 201 at one end of the container body 20A. The cap 30A includes an internal space S2. The space S2 has a size that can house one dental ceramic 40.

The cap 30A includes an outlet 31 in its side surface (outer surface) 30b. The outlet 31 has a size that allows the dental ceramic 40 to pass therethrough. The outlet 31 is formed to extend from a front inner surface 30c of the cap 30A in the axis direction of the cap 30A. The dental ceramic 40 can be taken out through the outlet 31.

The cap 30A is provided on the outer surface 20b of the container body 20A so as to be rotatable in the circumferential direction of the container body 20A. In the present embodiment, the groove 32 corresponding to the protrusion 22 of the container body 20A is formed on an inner surface 30a of the cap 30A. With the protrusion 22 fit into the groove 32, the cap 30A can rotate in the circumferential direction of the container body 20A.

The cap 30A is formed using a material having optical transparency. The cap 30A can be formed using a material similar to the material of the container body 20A, and therefore the description of the material is omitted here.

When the container body 20A is colorless, the cap 30A may be colored with a pigment so as to be distinguishable from the container body 20A. When the container body 20A is colored, the cap 30A may include a pigment different from a pigment used for the container body 20A. When the cap 30A is colored, the cap 30A is preferably colored to such a degree that transparency is maintained.

The cap 30A includes a pair of second holders 33A on the inner surface 30a. The pair of second holders 33A are arranged on the inner surface 30a of the cap 30A to face each other across the outlet 31. The surfaces of the second holders 33A facing the primary surfaces 40a and 40b of the dental ceramic 40 are made flat to be able to hold the primary surfaces 40a and 40b such that the dental ceramic 40 is movable. The pair of second holders 33A and the cap 30A are formed as a monolithic component. However, the second holders 33A may be produced as components separate from the cap 30A and attached to the inner surface 30a of the cap 30A using a bonding material such as an adhesive or a double-sided tape.

Because the cap 30A is rotatable in the circumferential direction of the container body 20A, when the cap 30A is seen in the axial direction, the pair of second holders 33A may be positioned such that the flat surfaces of the pair of second holders 33A become continuous with the flat surfaces of the pair of first holders 21. This makes it possible to form a continuous space in which the dental ceramic 40 is movable. That is, when the flat surfaces of the pair of first holders 21 become continuous with the flat surfaces of the pair of second holders 33A, the space S1 and the space S2 form a passage where the dental ceramic 40 is movable. Also, the positions of the pair of second holders 33A may be adjusted such that the flat surfaces of the pair of second holders 33A become not continuous with the flat surfaces of the pair of first holders 21 and the dental ceramic 40 becomes not movable in the space. In this case, the dental ceramic 40 is housed in the cap 30A between the second holders 33A such that the pair of primary surfaces 40a and 40b of the dental ceramic 40 face the second holders 33A.

When forming a space where the dental ceramic 40 is movable, the flat surfaces of the pair of first holders 21 do not necessarily completely match and are not necessarily completely continuous with the flat surfaces of the pair of second holders 33A. As long as a space where the dental ceramic 40 is movable is formed, the flat surfaces of the pair of first holders 21 may be misaligned with the flat surfaces of the pair of second holders 33A when the cap 30A is viewed in the axial direction.

Figure 7:
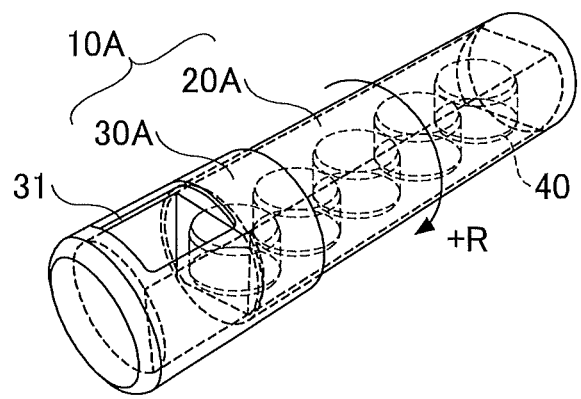
FIG. 7 is a drawing illustrating a method of taking out a dental ceramic from a dental material container.
Figure 7:
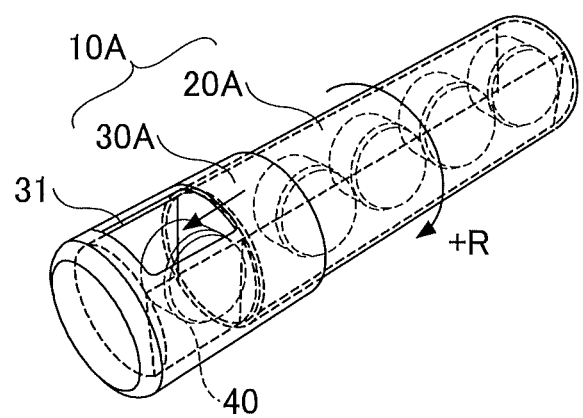
Figure 7:
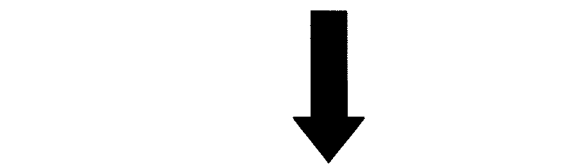
Figure 7:
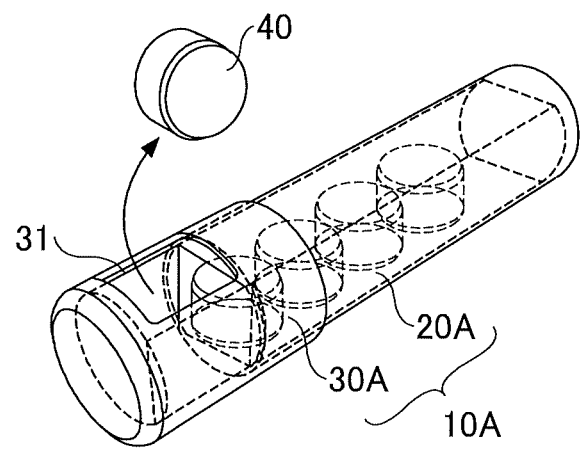
Figure 8:
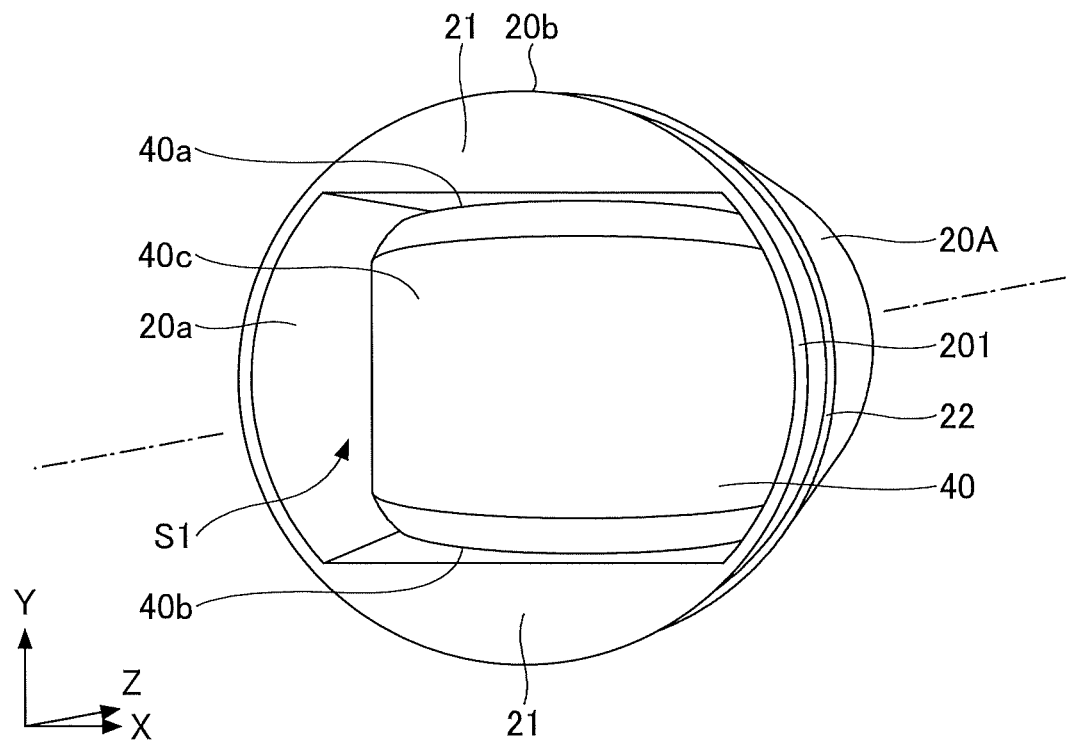
FIG. 8 is a drawing illustrating a state where a dental ceramic is stored in a container body.
Figure 9:
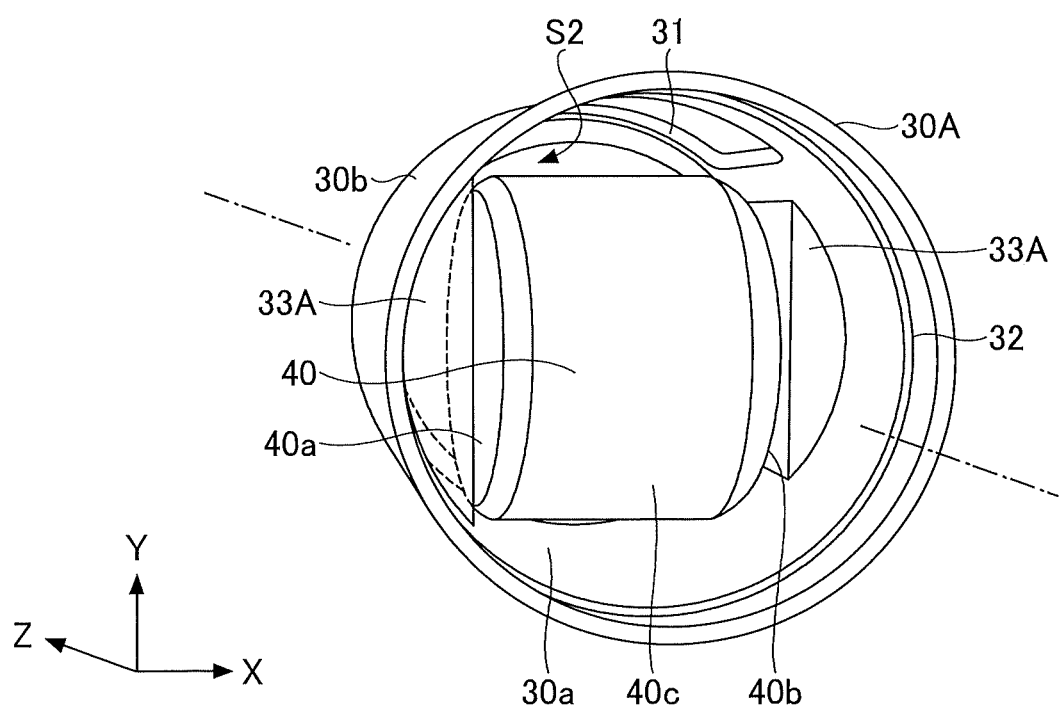
FIG. 9 is a drawing illustrating a state where a dental ceramic is moved to a cap.

An operation performed to take out the dental ceramic 40 from the dental material container 10A is described. As illustrated in FIG. 7, while the cap 30A is kept stationary, the container body 20A is rotated by a predetermined angle (e.g., 90 degrees) in one circumferential direction (+R direction) of the container body 20A to align the first holders 21 of the container body 20A with the second holders 33A of the cap 30A. As a result, the flat surfaces of the first holders 21 become continuous with the flat surfaces of the second holders 33A, and a continuous space is formed by the first holders 21 and the second holders 33A to allow movement. As a result, among the multiple dental ceramics 40 stored in the container body 20A, the dental ceramic 40 (see FIG. 8) located closest to the opening 201 in the container body 20A moves from the inside of the container body 20A to the inside of the cap 30A as illustrated in FIG. 7. Then, the dental ceramic 40 moved to the inside of the cap 30A is housed in the cap 30A with its primary surfaces 40a and 40b held by the pair of second holders 33A (see FIG. 9).

After the dental ceramic 40 is housed in the cap 30A, while the cap 30A is kept stationary, the container body 20A is further rotated by a predetermined angle (for example, 90 degrees) in one circumferential direction (+R direction) of the container body 20A to move the first holders 21 of the container body 20A out of alignment with the second holders 33A of the cap 30A. As a result, the movement of the dental ceramic 40 housed in the cap 30A into the container body 20A is restricted by the first holders 21, and the dental ceramic 40 held by the pair of second holders 33A is kept inside of the cap 30A.

Next, the dental material container 10A is oriented such that the outlet 31 faces downward to take out the dental ceramic 40 housed in the cap 30A. Even when the dental ceramic 40 housed in the cap 30A is taken out, because the flat surfaces of the first holders 21 are out of alignment with the flat surfaces of the second holders 33A, the dental ceramic 40 housed in the container body 20A does not move into the cap 30A.

Although the cap 30A is rotated in the +R direction by a predetermined angle in FIG. 7, the cap 30A may be rotated in a −R direction by a predetermined angle.

Also, although the cap 30A is kept stationary and the container body 20A is rotated in the circumferential direction of the container body 20A in FIG. 7, the container body 20A may be kept stationary, and the cap 30A may be rotated in the circumferential direction of the cap 30A. That is, the cap 30A may be rotated relative to the container body 20A in the circumferential direction of the container body 20A.

The dental material container 10A configured as described above includes the container body 20A and the cap 30A that, is rotatable in the circumferential direction of the container body 20A, a pair of first holders 21 are provided inside of the container body 20A, and a pair of second holders 33A are provided inside of the cap 30A. The cap 30A is rotated relative to the container body 20A in the circumferential direction of the container body 20A to form a continuous movement-enabling space by the pair of first holders 21 and the pair of second holders 33A so that the dental ceramic 40 in the container body 20A can move into the cap 30A and can be housed in the cap 30A. Accordingly, with the dental material container 10A, the dental ceramic 40 can be easily taken out of the container body 20A.

Also, with the dental material container 10A, after the dental ceramic 40 is housed in the cap 30A, the cap 30A is rotated in the circumferential direction relative to the container body 20A to move the flat surfaces of the first holders 21 out of alignment with the flat surfaces of the second holders 33A. With this configuration, the first holders 21 can prevent the dental ceramic 40 housed in the cap 30A from moving back into the container body 20A. Further, the configuration of the dental material container 10A can prevent a dental ceramic 40 housed in the container body 20A from moving into the cap 30A after the dental, ceramic 40 housed in the cap 30A is taken out. Thus, according to the dental material container 10A, the dental ceramics 40 stored in the container body 20A can be smoothly taken out one by one through the cap 30A.

Thus, with the dental material container 10A, it is possible to easily take out dental ceramics one by one during work.

Therefore, the dental material container 10A is suitable for a container for dental ceramics used when a prosthesis such as a veneer crown, an inner core, or a bridge is produced at a dental laboratory.

In the present embodiment, the container body 20A and the cap 30A are formed of a material having optical transparency. However, the container body 20A and the cap 30A may be formed of a material that does not have optical transparency. Here, not having optical transparency indicates that the container body 20A has such a visible light shielding property that the shape of the dental ceramics 40 in the container body 20A cannot be or is hardly visible from the outside.

Figure 10:
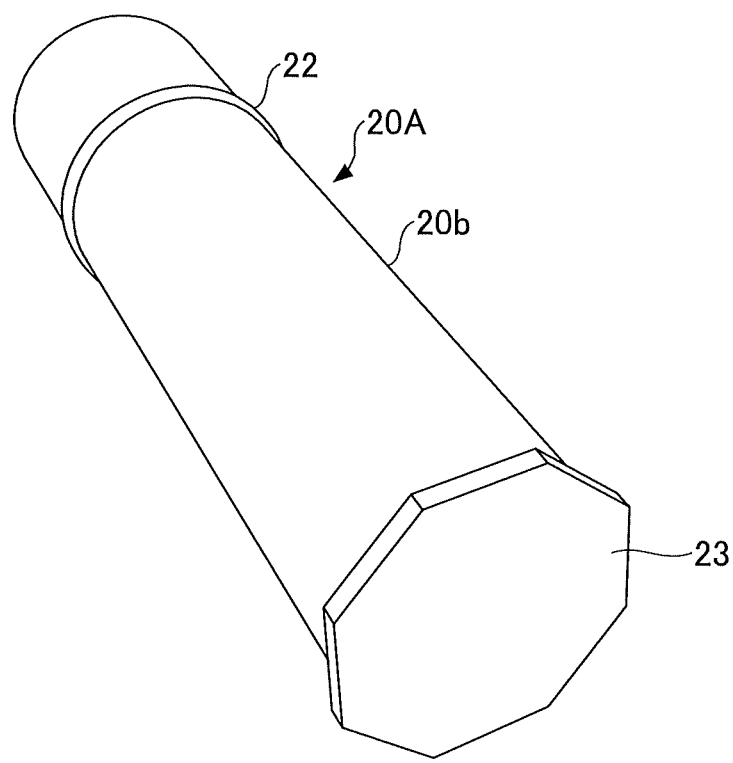
FIG. 10 is a perspective view of a variation of a container body.

In the present embodiment, the container body 20A and the cap 30A are shaped like circular cylinders. However, a part of the outer surface of one or both of the container body 20A and the cap 30A may be chamfered. Alternatively, portions of: the container body 20A and the cap 30A excluding joint portions may be formed as cylinders having a quadrangular shape when seen in the axial direction. Also, an anti-rotation part having a polygonal shape when seen in the axis direction of the container body 20A may be provided at an end of the container body 20A. In this case, the anti-rotation part is preferably formed such that the minimum outer diameter of the anti-rotation part is greater than or equal to the outer diameter of the container body 20A. Here, the minimum outer diameter indicates the length of the shortest one of diagonal lines representing outer diameters of the anti-rotation part. For example, as illustrated in FIG. 10, an anti-rotation part 23 having an octagonal shape when seen in the axial direction of the container body 20A and having an outer diameter greater than the outer diameter of the container body 20A may be formed at an end of the container body 20A. This configuration makes it possible to prevent the dental material container 10A from rolling when the dental material container 10A is placed on, for example, a work table.

Figure 11:
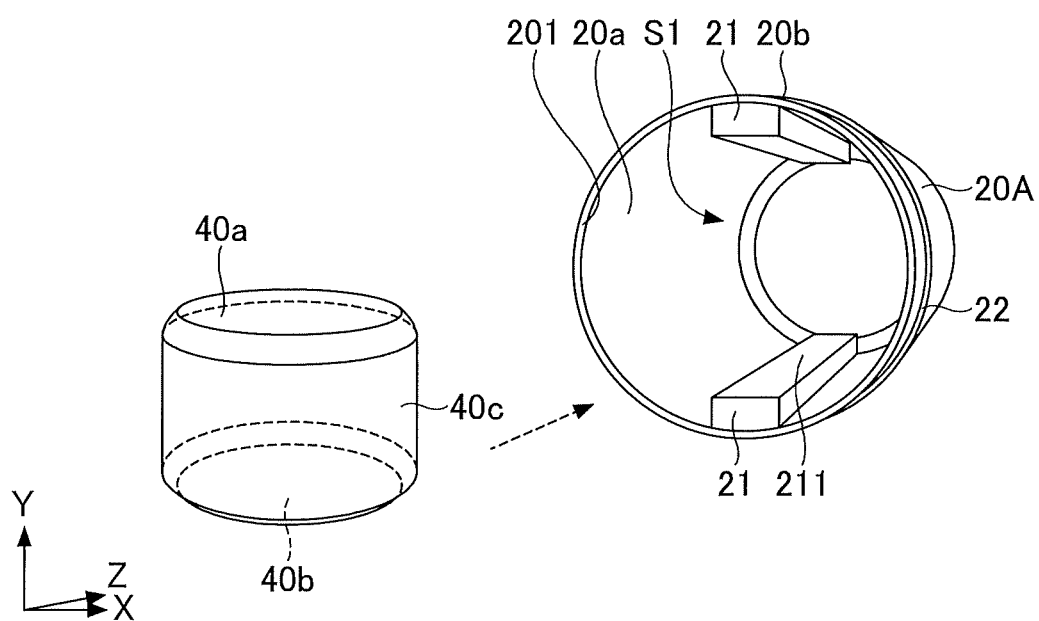
FIG. 11 is a perspective view of a variation of a first holder.
Figure 12:
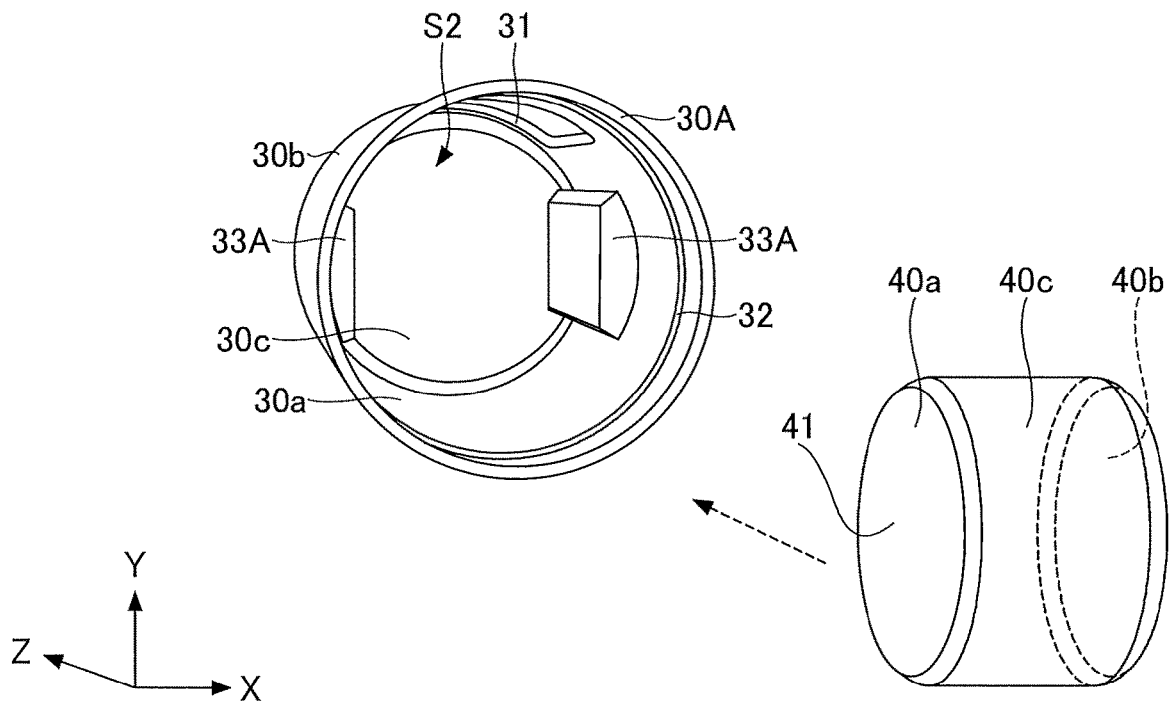
FIG. 12 is a perspective view of a variation of a second holder.
Figure 13:
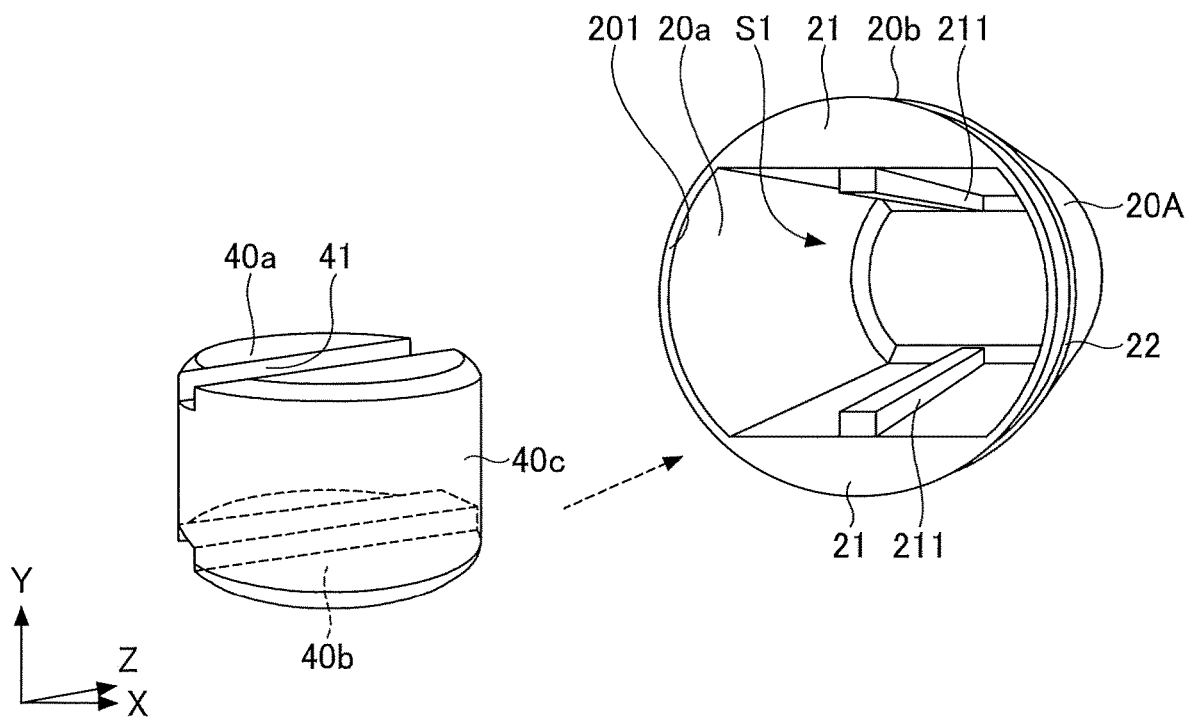
FIG. 13 is a perspective view of another variation of a first holder.
Figure 14:
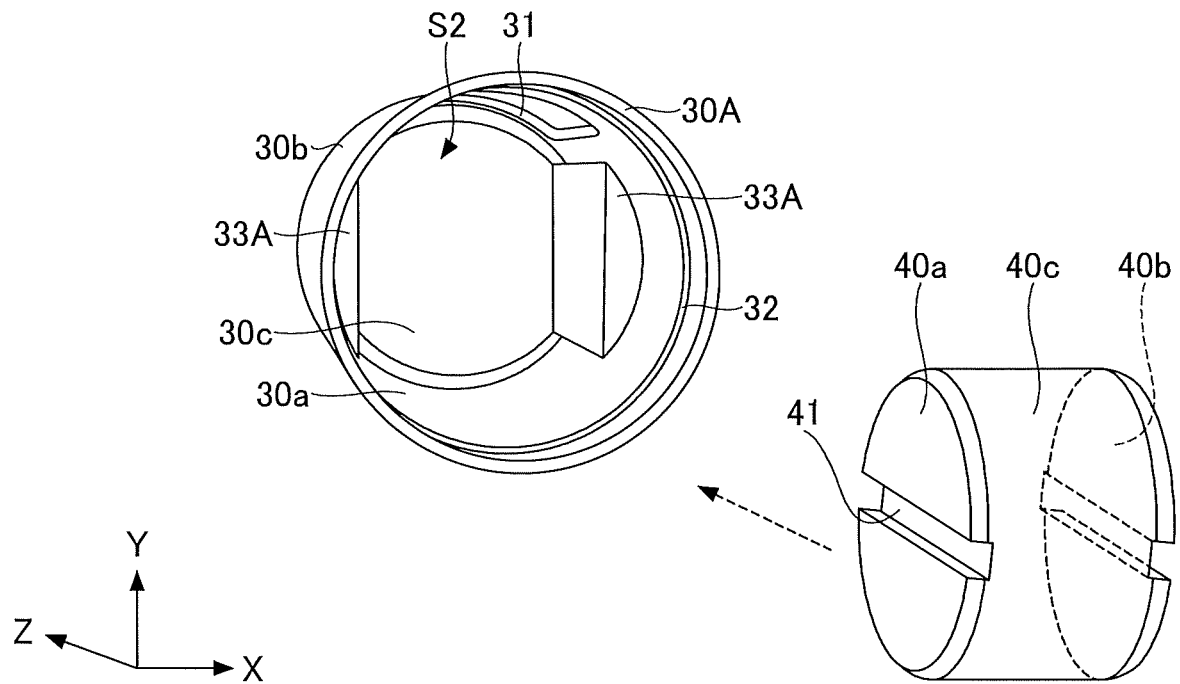
FIG. 14 is a perspective view of another variation of a second holder.

In the present embodiment, the first holders 21 and the second holders 33A have flat surfaces facing the primary surfaces 40a and 40b. However, the shapes of the first holders 21 and the second holders 33A are not limited to this example. The first holders 21 and the second holders 33A may be formed depending on the shapes of the primary surfaces 40a and 40b of the dental ceramic 40 to be able to hold the primary surfaces 40a and 40b of the dental ceramic 40 such that the dental ceramic 40 is movable. For example, as illustrated in FIGS. 11 and 12, rectangular first holders 21 may be formed on the inner surface 20a of the container body 20A along its axial direction, and rectangular second holders 33A may formed on the inner surface 30a of the cap 30A along its axial direction. Also, as illustrated in FIGS. 13 and 14, when the dental ceramic 40 includes recessed grooves 41 in the primary surfaces 40a and 40b, the first holders 21 may include protrusions 211 on the flat surfaces at positions facing the grooves 41. In this case, the second holders 33A may not include protrusions at positions facing the grooves 41.

In the present embodiment, the protrusion 22 is formed on the entire circumference of the outer surface 20b of the container body 20A along the circumferential direction of the container body 20A. However, the protrusion 22 may be formed at predetermined intervals in the circumferential direction of the outer surface 20b.

In the present embodiment, the dental ceramic 40 has a circular shape in plan view, but may have a quadrangular shape such as a rectangular shape or a square shape.

Second Embodiment

A dental material container according to a second embodiment is described. In a dental material container of the present embodiment, an extension part extending up to the inside of the cap is provided on the container body of the dental material container 10A of the first embodiment.

Figure 15:
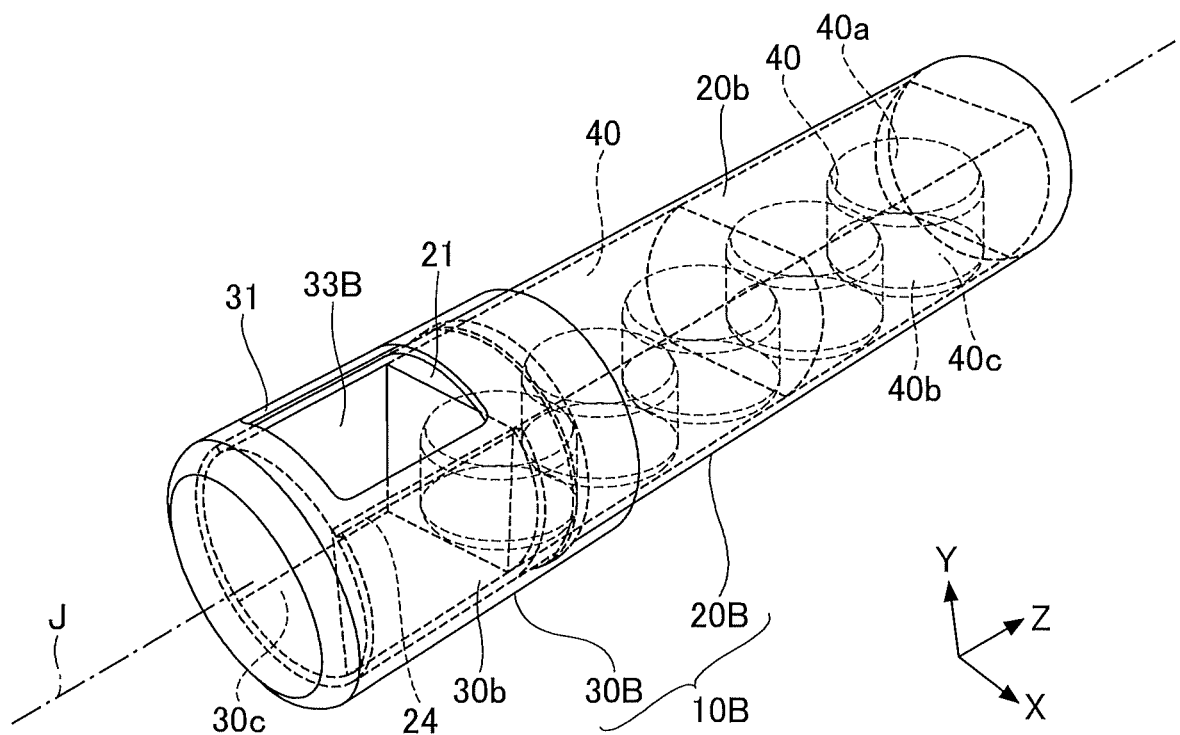
FIG. 15 is a perspective view of a dental material container according to a second embodiment.
Figure 16:
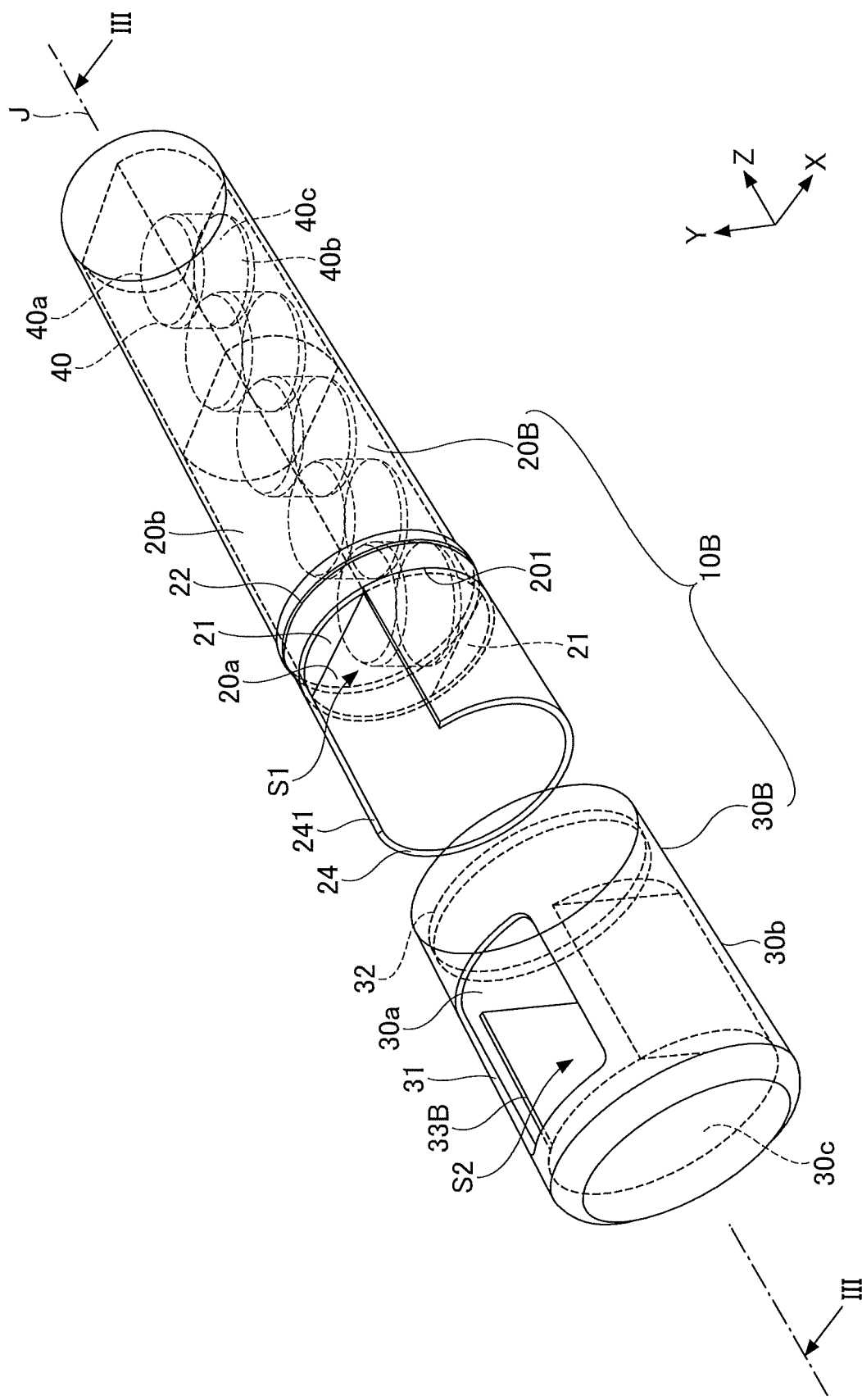
FIG. 16 is an exploded perspective view of a dental material container.

FIG. 15 is a perspective view of a dental material container according to the second embodiment, and FIG. 16 is an exploded perspective view of the dental material container. As illustrated in FIGS. 15 and 16, a dental material container 10B of the present embodiment includes an extension part 24 extending from an opening 201 of a container body 20B to the vicinity of a front inner surface 30c of a cap 30B.

A cutout part 241, which is an opening extending in the longitudinal direction of the container body 20B, is formed in a portion of the extension part 24. The cutout part 241 is large enough to allow the dental ceramic 40 to pass therethrough, and preferably has a size greater than or equal to the size of the outlet 31. Making the cutout part 241 larger than or equal to the outlet 31 makes it possible to prevent the cutout part 241 from blocking the dental ceramic 40 being taken out through the outlet 31.

Figure 17:
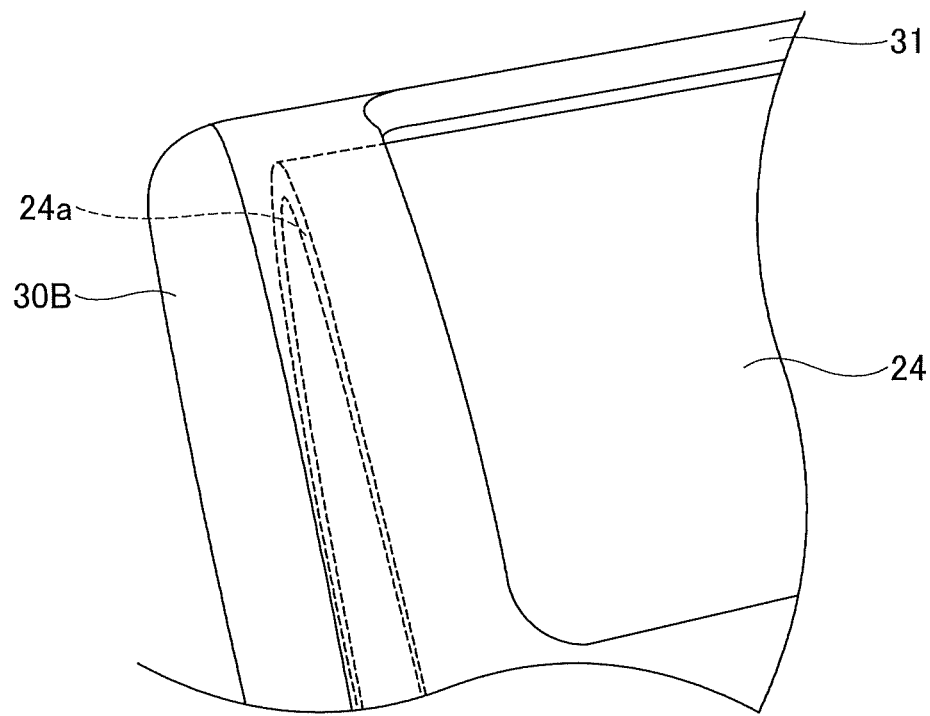
FIG. 17 is a drawing illustrating a state where a cap is rotated.
Figure 17:
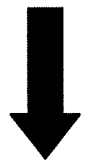
Figure 17:
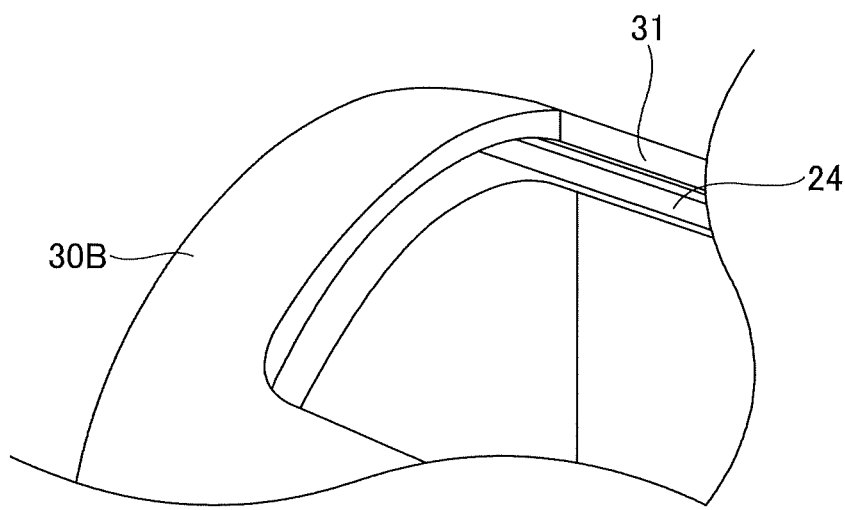

When the extension part 24 is seen along the longitudinal direction of the container body 20A, an end 24a of the extension part 24 in the −Z axis direction is located near the front inner surface 30c. Therefore, as illustrated in FIG. 17, when the cap 30B is rotated, the extension part 24 rotates along the inner surface 30a of the cap 30B so as to cover edges of the outlet 31 in the Z axis direction.

Figure 18:
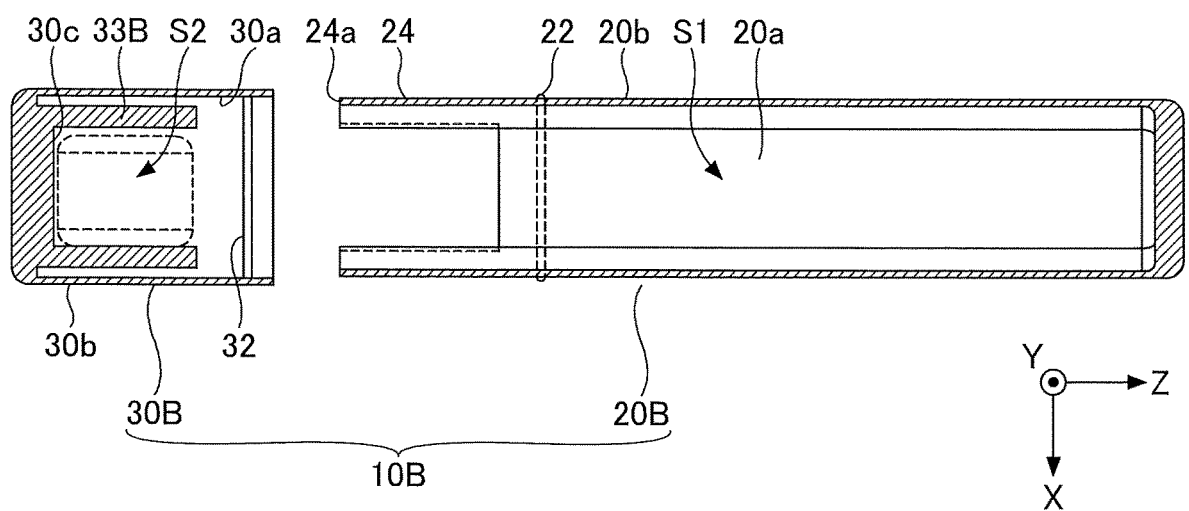
FIG. 18 is a cross-sectional view taken along line III-III of FIG. 16.

As illustrated in FIG. 18, second holders 33B are disposed apart from the inner surface 30a of the cap 30B. The second holders 33B are joined to the front inner surface 30c of the cap 30B. The extension part 24 is inserted between the inner surface 30a of the cap 30B and the second holders 33B. Along with the rotation of the container body 20B or the cap 30B, the extension part 24 can be kept in a state in which the extension part 24 is rotatably inserted between the inner surface 30a and the second holders 33B.

Figure 19:
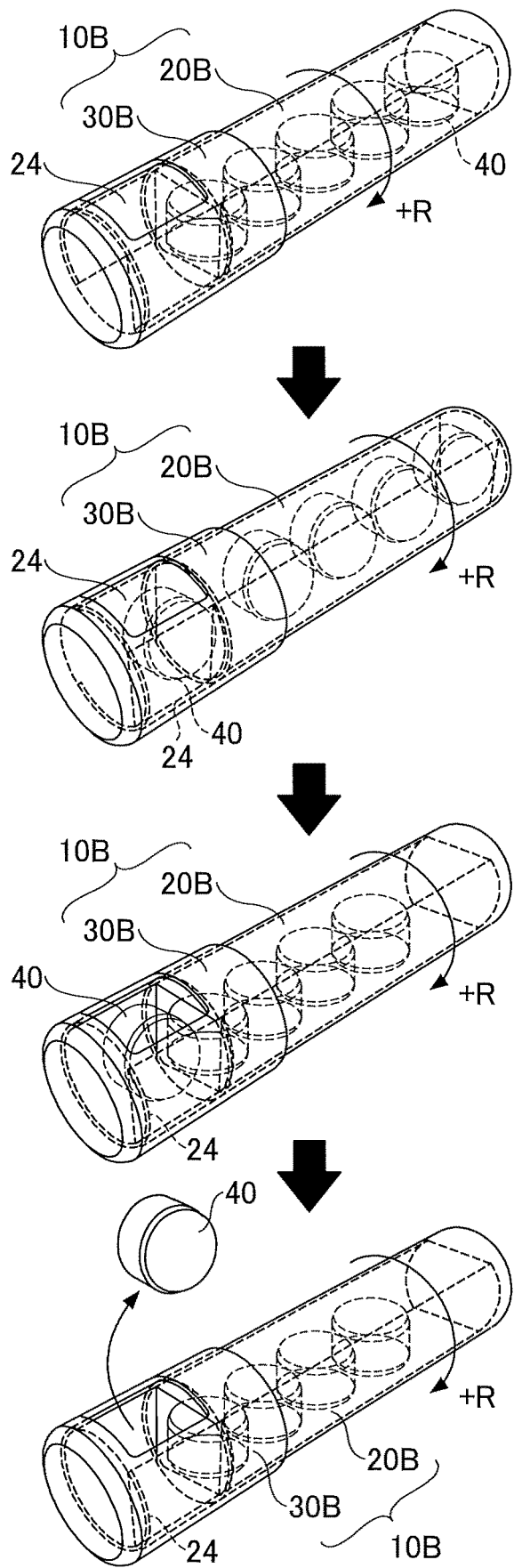
FIG. 19 is a drawing illustrating a method of taking out a dental ceramic from a dental material container.
Figure 20:
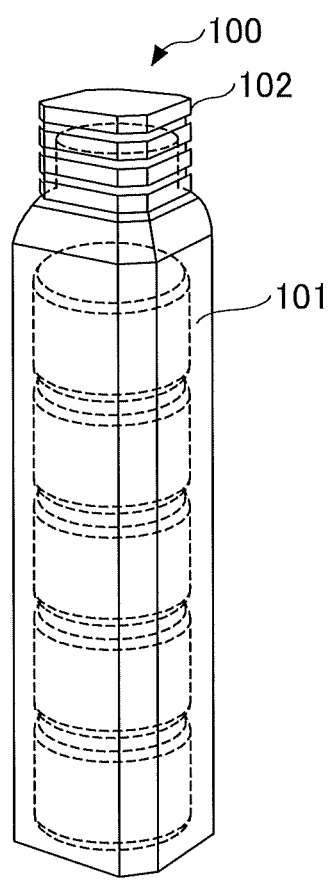
FIG. 20 is a perspective view of a related-art dental material container.

An operation performed to take out the dental ceramic 40 from the dental material container 10B is described. As illustrated in FIG. 19, while the cap 30B is kept stationary, the container body 20B is rotated by a predetermined angle (e.g., 90 degrees) in one circumferential direction (+R direction) of the container body 20B to align the first holders 21 of the container body 20B with the second holders 33B of the cap 30B. As a result, the flat surfaces of the first holders 21 become continuous with the flat surfaces of the second holders 33B, and a continuous space is formed by the first holders 21 and the second holders 33B to allow movement. As a result, among the multiple dental ceramics 40 stored in the container body 20B, the dental ceramic 40 located closest to the opening 201 in the container body 20B moves from the inside of the container body 20B to the inside of the cap 30B. Then, the dental ceramic 40 moved to the inside of the cap 30B is housed in the cap 30B with its primary surfaces 40a and 40b held by the pair of second holders 33B.

After the dental ceramic 40 is housed in the cap 30B, while the cap 30B is kept stationary, the container body 20B is further rotated by a predetermined angle (for example, 90 degrees) in one circumferential direction (+R direction). Because the extension part 24 rotates together with the container body 20B along with the rotation of the container body 20B, the container body 20B is rotated such that the cutout part 241 is aligned with the outlet 31. As a result, the dental ceramic 40 in the cap 30B is exposed to the outside. Also, the first holders 21 of the container body 20B become out of alignment with the second holders 33B of the cap 30B. Therefore, the first holders 21 of the container body 20B become out of alignment with the second holders 33B of the cap 30B, and the dental ceramic 40 housed in the cap 30B is prevented by the first holders 21 from moving back into the container body 20B. As a result, the dental ceramic 40 held by the pair of second holders 33A are kept inside of the cap 30B.

Next, the dental ceramic 40 is taken out of the cap 30B. Even when the dental ceramic 40 housed in the cap 30B is taken out, because the flat surfaces of the first holders 21 are out of alignment with the flat surfaces of the second holders 33B, a dental ceramic 40 housed in the container body 20B does not move into the cap 30B.

After the dental ceramic 40 is taken out of the cap 30B, while the cap 30B is kept stationary, the container body 20B is further rotated by a predetermined angle (for example, 180 degrees) in one circumferential direction (+R direction). As a result, the outlet 31 of the cap 30B is covered by the extension part 24 of the container body 20B.

In the dental material container 10B configured as described above, the container body 20B includes the extension part 24 extending from the opening 201 to the front inner surface 30c of the cap 30B, and the cutout part 241, which is an opening, is formed in a part of the extension part 24. With this configuration, when the dental material container 10B is unused and stored and the dental ceramics 40 in the container body 20B are not to be taken out, the extension part 24 can close the outlet 31 and prevent, for example, dust from entering through the outlet 31. Also, this configuration makes it possible to prevent the dental ceramic 40 moved into the cap 30B from coming out when the dental ceramic 40 is not to be used. Accordingly, the configuration of the dental material container 10B makes it possible to maintain high hygiene and prevent the dental ceramic 40 moved into the cap 30B from coming out when the dental ceramic 40 is not to be used.

In the present embodiment, the extension part 24 extends to the front inner surface 30c of the cap 30B. However, this is not essential, as long as the extension part 24 extends to a position inside of the cap 30B. For example, the extension part 24 may extend to the middle of the outlet 31.

The dental material containers 10A and 10B are described above based on an assumption that dental materials are dental ceramic molded bodies, and the configurations of the dental material containers 10A and 10B make it possible to easily take out dental materials such as dental ceramics. Apparently, the dental material containers 10A and 10B can be suitably used not only for dental ceramics but also for tablet-shaped medical drugs, sweets, and so on.

Although the embodiments are described above, the embodiments are presented as examples, and the present invention is not limited to the embodiments. The above embodiments may be implemented in various other manners, and combinations, omissions, replacements, and modifications may be made without departing from the spirit of the present invention. The above embodiments and their variations are included in the scope and the spirit of the present invention, and are also included in the invention described in the claims and the scope of equivalents.

The present, application claims priority to Japanese Patent Application No. 2018-059438 filed on Mar. 27, 2018, the entire contents of which are hereby incorporated herein by reference.

EXPLANATION OF REFERENCE NUMERALS 10A, 10B dental material container
20A, 20B container body
21 first holder
22 protrusion
24 extension part
30A, 30B cap
31 outlet
32 groove
33A, 33B second holder
40 dental ceramic

The invention claimed is:

1. A dental material container, comprising
a container body shaped like a cylinder with a bottom and configured to store a dental material that is shaped like a thick plate and includes a pair of opposing primary surfaces; and
a cap formed to cover an opening at one end of the container body, wherein
the cap is provided on the container body such that the cap is rotatable in a circumferential direction of the container body and includes an internal space capable of housing the dental material;
an outlet through which the dental material is taken out is formed in a side surface of the cap;
the container body includes a pair of first holders that are formed on an inner surface of the container body to hold the primary surfaces of the dental material such that the dental material is movable;
the cap includes a pair of second holders formed inside of the cap to hold the primary surfaces of the dental material such that the dental material is movable; and
the dental material container is configured such that when the cap is rotated in the circumferential direction relative to the container body, a continuous space where the dental material is movable is formed by the first holders and the second holders, the dental material located closest to the opening in the container body moves into the cap, and the dental material moved into the cap is housed in the cap.

2. The dental material container as claimed in claim 1, wherein the dental material container is configured such that when the cap is further rotated in the circumferential direction relative to the container body after the dental material is housed in the cap, the first holders become out of alignment with the second holders and the dental material housed in the cap is prevented by the first holders from moving into the container body.

3. The dental material container as claimed in claim 1, wherein
a protrusion is formed on an outer surface of the container body;
a groove corresponding to the protrusion is formed in an inner surface of the cap; and
the protrusion is configured to be fit in the groove.

4. The dental material container as claimed in claim 1, wherein
the container body includes an extension part extending from the opening to an inside of the cap; and
a cutout part, which is an opening extending in a longitudinal direction of the container body, is formed in a portion of the extension part.

5. The dental material container as claimed in claim 4, wherein
the second holders are disposed apart from an inner surface of the cap; and the extension part is inserted between the inner surface and the second holders.

6. The dental material container as claimed in claim 1, wherein the dental material is a dental ceramic.

\* \* \* \* \*